US008729027B2

(12) United States Patent
Nishioka

(10) Patent No.: US 8,729,027 B2
(45) Date of Patent: May 20, 2014

(54) THERAPEUTIC AGENT FOR FIBROMYALGIA CONTAINING ETANERCEPT

(75) Inventor: Kusuki Nishioka, Tokyo (JP)

(73) Assignee: AXIS Inc., Kagoshima (JP)

( * ) Notice: Subject to any disclaimer, the term of this patent is extended or adjusted under 35 U.S.C. 154(b) by 0 days.

(21) Appl. No.: 13/808,291

(22) PCT Filed: Jul. 4, 2011

(86) PCT No.: PCT/JP2011/003797

§ 371 (c)(1), (2), (4) Date: Jan. 4, 2013

(87) PCT Pub. No.: WO2012/004966

PCT Pub. Date: Jan. 12, 2012

(65) Prior Publication Data

US 2013/0108637 A1 May 2, 2013

(30) Foreign Application Priority Data

Jul. 5, 2010 (JP) ................................ 2010-153504

(51) Int. Cl.

*A61P 23/00* (2006.01)
*A61K 38/00* (2006.01)
*C07K 14/52* (2006.01)
*C07K 14/715* (2006.01)

(52) U.S. Cl.

USPC ........................... 514/18.3; 530/350; 930/144

(58) Field of Classification Search

None

See application file for complete search history.

(56) References Cited

U.S. PATENT DOCUMENTS 6,982,089 B2 * 1/2006 Tobinick ........................ 424/400
2002/0165246 A1 * 11/2002 Holman ........................ 514/270

* cited by examiner

*Primary Examiner* — Zachary Howard
(74) *Attorney, Agent, or Firm* — Osha Liang LLP

(57) ABSTRACT

Disclosed is a drug effective in the treatment of fibromyalgia. Basically, the disclosed therapeutic agent was created on the basis of experiments showing improvement in symptoms when etanercept was administered to patients suffering from fibromyalgia. Etanercept is known as a therapeutic agent for rheumatoid arthritis, and the JFIQ score of patients not suffering from fibromyalgia improved considerably in the preferred embodiment. In other words, a therapeutic agent for fibromyalgia is disclosed that contains etanercept as an active ingredient in an effective amount.

3 Claims, No Drawings

THERAPEUTIC AGENT FOR FIBROMYALGIA CONTAINING ETANERCEPT

TECHNICAL FIELD

The present invention relates to a therapeutic agent for fibromyalgia, which contains etanercept as an active ingredient.

BACKGROUND ART

Fibromyalgia is a disease which develops, for example, unexplained pains, insomnia, neuropsychiatric symptoms, irritable bowel syndrome and cystitis as prominent symptoms. In recent years, fibromyalgia, which is accompanied by mucosal system disorders (dry eye, dry mouth) and enthesitis, have been discovered. Meanwhile, the cause of fibromyalgia has not been revealed. Therefore, therapeutic agents for fibromyalgia are demanded now.

For example, WO 2008-041751 A1 discloses a therapeutic agent for fibromyalgia accompanied by enthesitis, which contains salazosulfapyridine as an active ingredient.

WO 2007-052125 A2 discloses a therapeutic agent for hypermyotonia-type fibromyalgia, which contains pregabalin as an active ingredient.

WO 2009-139470 A1 discloses a therapeutic agent for hypermyotonia-type fibromyalgia, which contains pilocarpin hydrochloride as an active ingredient.

Meanwhile, etanercept is manufactured and sold under the trade name "Enbrel" (registered trademark) as a therapeutic agent for rheumatoid arthritis (an attached document of "Enbrel" (registered trademark) for subcutaneous injection). Etanercept is a soluble TNF receptor (JP 2721745 B2, JP 2728968 B2, and JP 2960039 B2).

Non-Patent Literature 2 (ORTEGA, E. et al, Aquatic exercise improves the monocyte pro- and anti-inflammatory cytokine production balance in fibromyalgia patients, Scand J Med Sci Sports, 2010, Vol. 1193, No. 1, p. 1-9) shown below discloses a hypothesis that the amount of an inflammatory cytokine, such as a TNFα, risesin fibromyalgia patients (excluding rheumatoid patients). However, this matter is just a hypothesis, and it is not mentioned that the reasons for the increase of the amount of an inflammatory cytokine such as a TNFα in certain fibromyalgia patient is associated with fibromyalgia. In Non-Patent Literature 2, it is not demonstrated that an inflammatory cytokine such as TNFα is a cause of pains in fibromyalgia. In Non-Patent Literature 2, nothing is disclosed about a knowledge concerning the increase or decrease in TNFα levels and fibromyalgia. Further, in Non-Patent Literature 2, it is not demonstrated in any way that the inhibition of an inflammatory cytokine such as TNFα is effective for the amelioration of pains in fibromyalgia and the like.

In Wyeth Kabushiki Kaisha, Enbrel 25 mg for subcutaneous injection, Interview form for pharmaceuticals, 2007, 6th edition, 1-57 (Non-Patent Literature 3 shown below), it is described that etanercept has an inhibitory activity on TNFα and that etanercept is effective for the treatment of inflammation-dependent pains in rheumatoid or the like, and an etanercept-containing preparation for injection is disclosed.

CITATION LIST

Patent Literature

Patent Literature 1: WO 2008-041751 A1
Patent Literature 2: WO 2007-052125 A2

Patent Literature 3: WO 2009-139470 A1
Patent Literature 4: JP 2721745 B2
Patent Literature 5: JP 2728968 B2
Patent Literature 6: JP 2960039 B2

Non-Patent Literature

Non-Patent Literature 1: an attached document of Enbrel (registered trademark) for subcutaneous injection Non-Patent Literature 2: ORTEGA, E. et al, Aquatic exercise improves the monocyte pro- and anti-inflammatory cytokine production balance in fibromyalgia patients, Scand J MedSci Sports, 2010, Vol. 1193, No. 1, p. 1-9

Non-Patent Literature 3: Wyeth Kabushiki Kaisha, Enbrel 25 mg for subcutaneous injection, Interview form for pharmaceuticals, 2007, 6th edition, 1-57

SUMMARY OF INVENTION

Technical Problem

An object of the present invention is to provide a drug which is effective for the treatment of fibromyalgia. An object of the present invention is to provide a drug which is effective for the treatment of enthesitis-type fibromyalgia.

Solution to Problem

The present invention is based on the experiments which revealed that the administration of etanercept can provide symptomatic relief with patients suffering from fibromyalgia.

Therefore, the present invention relates to a therapeutic agent for fibromyalgia, which contains etanercept as an active ingredient in an effective amount.

The present invention also provides a therapeutic agent used for the treatment of fibromyalgia, which contains etanercept as an active ingredient. The drug may be a pharmaceutical composition including the active ingredient and a pharmaceutically acceptable carrier. The present invention also provides a method for treating fibromyalgia by administering a drug containing etanercept as an active ingredient to the human body or non-human mammals.

The therapeutic agent according to the present invention preferably can be the injectable solution because the agent used in Example was also injectable solutions. Further, as demonstrated in Example, the therapeutic agent according to the present invention was effective for the treatment of fibromyalgia in a patient who is not suffering from rheumatoid (particularly rheumatoid arthritis). Therefore, the present invention also provides a method for treating fibromyalgia by administering a drug containing etanercept as an active ingredient to a patient who is not suffering from rheumatoid (particularly rheumatoid arthritis).

The therapeutic agent in the present invention is particularly effective to at least one symptom selected from a feeling of fatigability, sleep disorder, body temperature abnormality, psychroesthesia in hands and feet, numbness in arms and legs, excess sweating, a depressed condition, car sickness and menstrual irregularity all of which are associated with fibromyalgia. That is, the present invention also provides a method for ameliorating at least one symptom selected from a feeling of fatigability, sleep disorder, body temperature abnormality, psychroesthesia in hands and feet, numbness in arms and legs, excess sweating, a depressed condition, car sickness and menstrual irregularity all of which are associated with fibromyalgia by administering therapeutic agent containing etanercept as an active ingredient.

Advantageous Effects of Invention

The therapeutic agent according to the present invention contains etanercept as an active ingredient and can ameliorate symptoms of fibromyalgia, as demonstrated in Example.

DESCRIPTION OF EMBODIMENTS

The present invention relates to a therapeutic agent for fibromyalgia, which contains etanercept as an active ingredient in an effective amount (referred to as "a drug according to the present invention", hereinafter). Fibromyalgia which occurs as a sole symptom is called "primary fibromyalgia", and fibromyalgia which occurs in association with other diseases is called "secondary fibromyalgia". Examples of the primary diseases for secondary fibromyalgia include rheumatoid arthritis, rheumatic diseases (including Sjogren syndrome and systemic lupus erythematosus), interstitial cystitis and osteoarthritis.

The drug according to the present invention can alleviate various symptoms of fibromyalgia. The drug according to the present invention is effective for the treatment of enthesitis-type fibromyalgia, hypermyotonia-type fibromyalgia or depression-type fibromyalgia, among various symptoms of fibromyalgia.

The drug according to the present invention is not intended particularly for the amelioration of inflammations, and is effective for the amelioration of various symptoms induced by fibromyalgia. Therefore, the drug according to the present invention is particularly effective for the treatment of a patient with fibromyalgia that is not accompanied by any inflammation. Examples of such fibromyalgia include hypermyotonia-type fibromyalgia and depression-type fibromyalgia. The drug according to the present invention is effective for the amelioration of, for example, numbness, dizziness, a feeling of floating, sleep disorder, a feeling of anxiety, depression, a feeling of impatience, impairment of concentration, amnesia, sleep apnea and disturbance of consciousness all of which are associated with fibromyalgia. As demonstrated in Example mentioned below, the drug according to the present invention is particularly effective for the amelioration of a feeling of fatigability, sleep disorder, body temperature abnormality, psychroesthesia in hands and feet, numbness in arms and legs, excess sweating, depressed condition, car sickness and menstrual irregularity all of which are associated with fibromyalgia. Therefore, the drug according to the present invention is effective for the amelioration of at least one fibromyalgia-related symptom selected from these symptoms.

Etanercept is also commercially available as "Enbrel" (registered trademark). Therefore, etanercept which is an active ingredient for the drug according to the present invention is publicly known. The drug according to the present invention can be formulated into a preparation by any one of known techniques. The drug according to the present invention may be a drug similar to "Enbrel" (registered trademark).

Etanercept is a recombinant TNF-R protein which is disclosed in JP 2960039 B2. Etanercept can be produced by the method disclosed in JP 2960039 B2. Etanercept is a polypeptide produced by the dimerization of amino acid monomers each composed of 467 amino acid residues and is therefore composed of 934 amino acid residues (sometimes referred to as "the peptide according to the present invention", hereinafter). The active ingredient of the drug according to the present invention to be used may be a polypeptide which is produced by deleting, substituting, inserting or adding one or several amino acid residues in the peptide according to the present invention and which has a therapeutic effect on fibromyalgia. The active ingredient of the drug according to the present invention may also be a pharmaceutically acceptable salt of the peptide according to the present invention. The active ingredient of the drug according to the present invention may also consist of the peptide according to the present invention and other substances combined with the peptide.

The preparation form (dosage form) of the drug according to the present invention may be any form of publicly known ones, as long as the dosage form enables the active ingredient to reach an affected part. Examples of the dosage form of the drug according to the present invention include an oral preparation and an injectable preparation. The drug according to the present invention may have a dosage form of a solid preparation or a liquid preparation. An example of the oral preparation is a tablet. The tablet can be produced by compressing a raw material containing the active ingredient using a tableting machine. The injectable preparation also contains water for injection, a sugar alcohol (e.g., D-mannitol), an organic amine (e.g., trometamol) and a buffering agent (e.g., hydrochloric acid), for example. The drug according to the present invention may also contain pharmaceutically acceptable carriers. Examples of the pharmaceutically acceptable carriers include a sustained-release carrier, a sugar, a sugar alcohol and water. The drug according to the present invention may also contain pharmaceutically acceptable additives. Examples of the pharmaceutically acceptable additives include an excipient, a diluent, a bulking agent, a disintegrating agent, a stabilizing agent, a preserving agent, a buffering agent, an emulsifying agent, a flavoring agent, a coloring agent, a sweetening agent, a thickening agent, a taste-control agent, a dissolution aid, a coating agent and a binder.

The dosage of the drug according to the present invention can be determined with taking the routes of administration and the ages and body weights of patients into consideration. In the case of an oral preparation, the dosage of the drug according to the present invention falls, for example, within the range from 10 mg to 10 g inclusive per day in terms of the content of etanercept. In the case of an injectable preparation, the unit dosage of the drug according to the present invention falls, for example, within the range from 1 mg to 100 mg inclusive and may fall within the range from 5 mg to 50 mg inclusive.

The conditions of fibromyalgia and the therapeutic effects on fibromyalgia can be determined in accordance with J-FIQ (FIQ of Japanese version; Fibromyalgia Impact Questionaive) (see Research group granted by the ministry of health labor and welfare, "Guidelines for diagnosis of fibromyalgia 2009", issued by Japan Rheumatism Foundation on 31 Mar. 2010, p. 58).

Example 1

Treatment of Fibromyalgia with Etanercept (Dosage: 10 mg)

"Enbrel (registered trademark), which is a commercially available etanercept preparation, was administered to patient A (age: 62, female, JFIQ score at the time of initiation of diagnosis: 48.9), patient B (age: 38, male, pain spots: right side of the body, JFIQ score at the time of initiation of diagnosis: 81.8), patient C (age: 49, female, pain spots: 5, JFIQ score at the time of initiation of diagnosis: 78.7) and patient D (age: 59, female, pain spots: 4, JFIQ score at the time of initiation of diagnosis: 56.6), who were diagnosed as being suffering from fibromyalgia, by subcutaneous injection, and the conditions of the patients were monitored over time. The patients did not suffer from rheumatoid. The dosage of etanercept to each of the patients was 10 mg.

Four weeks after the one-time administration of "Enbrel" (registered trademark), the JFIQ scores were determined again. As a result, it was found that the JFIQ scores for patient A, patient B, patient C and patient D were 16.9, 31.8, 46.7 and 27.0, respectively. In Table 1, the changes in JFIQ scores for the patients are shown.

TABLE 1

| Patients | Sex | Age | JFIQ at the Time of Initiation | JFIQ After Administration | JFIQ (After Administration)/(at the Time of Initiation) |
|---|---|---|---|---|---|
| Patient A | F | 62 | 48.9 | 16.9 | 0.346 |
| Patient B | M | 38 | 81.8 | 31.8 | 0.389 |
| Patient C | F | 49 | 78.7 | 46.7 | 0.593 |
| Patient D | F | 59 | 56.6 | 25 | 0.442 |

As shown in Table 1, in the patients to whom etanercept was administered, the amelioration of fibromyalgia was clearly observed. Fibromyalgia is sometimes accompanied by rheumatoid including rheumatoid arthritis and Sjogren syndrome. However, these patients were not affected by rheumatoid. Therefore, this experiment clearly demonstrates that etanercept is also effective for the treatment of fibromyalgia that is not accompanied by rheumatoid.

Particularly, the improvement in JFIQ scores greatly relied on the amelioration of a feeling of fatigability, sleep disorder, body temperature abnormality, psychroesthesia in hands and feet, numbness in arms and legs, excess sweating, depressed condition, car sickness and menstrual irregularity. Consequently, it is considered that the drug according to the present invention is effective for the amelioration of these symptoms.

Particularly, the results of this example demonstrate that etanercept is effective for the amelioration of various symptoms of inflammation-unrelated fibromyalgia and the treatment of various symptoms of inflammation-unrelated fibromyalgia.

INDUSTRIAL APPLICABILITY

The present invention can be used as a therapeutic agent for fibromyalgia in the pharmaceutical industry.

The invention claimed is:

1. A method of treating a patient who suffers from fibromyalgia, the method comprising a step of administering an agent comprising etanercept as an active ingredient in an effective amount to the patient, wherein the patient does not suffer from rheumatism.

2. The method in accordance with claim 1, wherein the agent has a dosage form of an injectable preparation.

3. The method in accordance with claim 1, the agent is administered to ameliorate at least one symptom associated with fibromyalgia selected from the group consisting of a feeling of fatigability, sleep disorder, body temperature abnormality, numbness in a hand or a foot, numbness in arms and legs, excess sweating, a depressed condition, car sickness, and menstrual irregularity.

* * * * *